United States Patent [19]
Ueno

[11] Patent Number: 5,537,163
[45] Date of Patent: Jul. 16, 1996

[54] OPHTHALMOLOGIC APPARATUS WITH AUTOMATIC FOCUSING USING TWO REFERENCE MARKS AND HAVING AN IN-FOCUS DETECTING SYSTEM

[75] Inventor: Yasunori Ueno, Kanagawa-ken, Japan

[73] Assignee: Nikon Corporation, Tokyo, Japan

[21] Appl. No.: 462,602

[22] Filed: Jun. 5, 1995

[30] Foreign Application Priority Data

Jun. 17, 1994 [JP] Japan .................. 6-159576

[51] Int. Cl.⁶ .................................................. A61B 3/14
[52] U.S. Cl. .................. 351/206; 351/208; 351/211
[58] Field of Search .................................. 351/206, 208, 351/211, 221

[56] References Cited

U.S. PATENT DOCUMENTS

| | | | |
|---|---|---|---|
| 4,400,070 | 8/1983 | Isono et al. | 351/208 |
| 4,673,264 | 6/1987 | Takahashi | 351/208 |
| 4,712,894 | 12/1987 | Nunokawa | 351/208 |
| 4,744,648 | 5/1988 | Kato et al. | 351/208 |

FOREIGN PATENT DOCUMENTS 61-122837   6/1986   Japan .
2285105    11/1993   Japan ................. 351/221

Primary Examiner—William L. Sikes
Assistant Examiner—James A. Dudek
Attorney, Agent, or Firm—Armstrong, Westerman, Hattori, McLeland & Naughton

[57] ABSTRACT

An ophthalmologic apparatus is provided with an illuminating optical system for illuminating a fundus oculi of an inspected eye with an illuminating light, a photographing and observing optical system for photographing and observing the fundus oculi of the inspected eye illuminated with the illuminating light by the illuminating optical system, a reference mark projecting optical system for projecting a reference mark on the fundus oculi of the inspected eye, an in-focus detecting optical system for detecting an in-focus condition between the photographing and observing optical system and the fundus oculi of the inspected eye by receiving an image of the reference mark projected on the fundus oculi of the inspected eye by the reference mark projecting optical system, and positional adjustment detecting optical system for detecting a positional adjustment between the ophthalmologic apparatus and the inspected eye by receiving a beam of light which is radiated from the reference mark projecting optical system and is reflected by a cornea of the inspected eye. The reference mark projecting optical system has a light source for radiating a beam of infrared light and/or a beam of near infrared light.

7 Claims, 3 Drawing Sheets

| | | |
|---|---|---|
| ◐ | | IN DESIRED POSITIONAL RELATIONSHIP |
| ◐ | ◐ | OUT OF DESIRED POSITIONAL RELATIONSHIP |

OPHTHALMOLOGIC APPARATUS WITH AUTOMATIC FOCUSING USING TWO REFERENCE MARKS AND HAVING AN IN-FOCUS DETECTING SYSTEM

BACKGROUND OF THE INVENTION

The present invention relates generally to an ophthalmologic apparatus, and more particularly to an ophthalmologic apparatus such as a retinal camera having an in-focus detecting optical system and a positioning detecting optical system.

In a prior art in which a conventional ophthalmologic apparatus such as a retinal camera is utilized, a fundus oculi of an inspected eye is illuminated with a beam of inspection light, a beam of light reflected by the fundus oculi is detected, and the fundus oculi of the inspected eye is observed or photographed.

However, in case of the conventional ophthalmologic apparatus, a reflection coefficient of the fundus oculi for the inspection light is low. Therefore, a quantity of the light reflected by the fundus oculi is not sufficient to observe the fundus oculi. Also, a contrast of the taken image of the fundus oculi on the inspected eye deteriorates. As a result, there is a problem that it is difficult to focus the fundus oculi of the inspected eye with an observation optical system or a photography optical system of the ophthalmologic apparatus.

Also, when a positional relationship between the inspected eye and the ophthalmologic apparatus undesirably changes, a flare caused by reflection of the inspected light on a cornea or a crystalline lens of the inspected eye is apt to enter the ophthalmologic apparatus. Therefore, the visibility of the image of the fundus oculi observed or photographed considerably deteriorates. As a result, there is another problem that a skilled operator is necessarily required to adjust the positional relationship between the inspected eye and the ophthalmologic apparatus on condition that any flare is not incident on the ophthalmologic apparatus.

SUMMARY OF THE INVENTION

An object of the present invention is to provide, with due consideration to the problems of such a conventional ophthalmologic apparatus, an ophthalmologic apparatus in which a positional relationship between the inspected eye and the ophthalmologic apparatus is easily adjusted; an in-focus condition of the ophthalmologic apparatus for the fundus oculi of the inspected eye is easily detected; and a fundus oculi photograph having a superior visibility is obtained.

The object is achieved by the provision of an ophthalmologic apparatus, comprising:

an illuminating optical system for illuminating a fundus oculi of an inspected eye with an illuminating light;

a photographing and observing optical system for photographing and observing the fundus oculi of the inspected eye illuminated with the illuminating light by the illuminating optical system;

a reference mark projecting optical system for projecting a reference mark on the fundus oculi of the inspected eye;

in-focus information detecting means for detecting a piece of in-focus information denoting that the photographing and observing optical system is just focused on the fundus oculi of the inspected eye by receiving an image of the reference mark projected on the fundus oculi of the inspected eye by the reference mark projecting optical system; and positional adjustment information detecting means for detecting a piece of positional adjustment information denoting a positional adjustment between the ophthalmologic apparatus and the inspected eye by receiving a beam of light which is radiated from the reference mark projecting optical system and is reflected by a cornea of the inspected eye.

In the above configuration of the ophthalmologic apparatus, the reference mark projected on the fundus oculi of the inspected eye by the reference mark projecting optical system is received by the in-focus information detecting means, and a piece of in-focus information denoting that the photographing and observing optical system is just focused on the fundus oculi of the inspected eye is detected by the in-focus information detecting means. Also, a beam of light which is radiated from the reference mark projecting optical system and is reflected by a cornea of the inspected eye is received by the positional adjustment information detecting means, and a piece of positional adjustment information denoting a positional adjustment between the ophthalmologic apparatus and the inspected eye is detected by the positional adjustment information detecting means.

Therefore, an in-focus detecting optical system represented by the in-focus information detecting means and a positional adjustment detecting system represented by the positional adjustment information detecting means have a projecting optical system represented by the reference mark projecting optical system for common use. In other words, the in-focus detecting optical system and the positional adjustment detecting system use a common detecting light source. As a result of the common use of the detecting light source (that is, a projecting optical system for detection), the constitution of the ophthalmologic apparatus can be simplified, and the detection of the in-focus information and the positional adjustment information can be easily and rapidly performed.

In a preferred modification according to the present invention, the positional adjustment information detecting means comprises:

a pupil dividing diaphragm for dividing the beam of light, which is radiated from the reference mark projecting optical system and is reflected by the cornea of the inspected eye, into two beams of light; and observing means for observing the two beams of light divided by the pupil dividing diaphragm.

In addition, it is preferred that the two beams of light which are divided by the pupil dividing diaphragm and overlaps with each other are observed by the observing means of the positional adjustment information detecting means on such a condition that a desired positional adjustment between the ophthalmologic apparatus and the inspected eye is detected by the positional adjustment information detecting means.

DESCRIPTION OF THE PREFERRED EMBODIMENTS

Preferred embodiments of an ophthalmologic apparatus according to the present invention are described with reference to the drawings.

Figure 1:
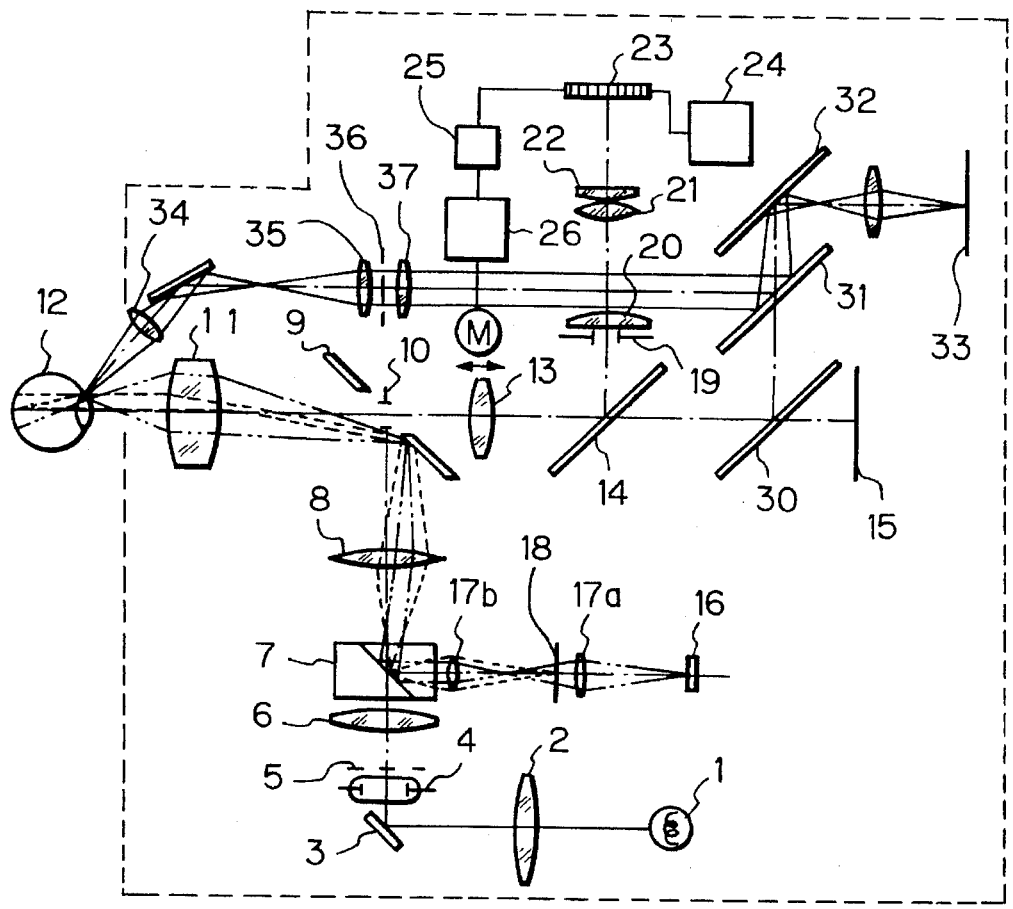
FIG. 1 is a schematic illustration showing the constitution of an ophthalmologic apparatus according to an embodiment of the present invention.

FIG. 1 is a schematic illustration showing the constitution of an ophthalmologic apparatus according to an embodiment of the present invention. An ophthalmologic apparatus shown in FIG. 1 comprises an illuminating optical system for illuminating a fundus oculi of an inspected eye, a reference mark projecting optical system for projecting a reference mark on the fundus oculi of the inspected eye, an in-focus detecting optical system for performing an in-focus detection for the fundus oculi of the inspected eye by receiving a beam of the light of the reference mark reflected by the fundus oculi of the inspected eye, a positional adjustment detecting optical system for detecting a positional adjustment between the ophthalmologic apparatus and the inspected eye, an observing optical system for observing a condition of the fundus oculi of the inspected eye, and a photographing optical system for photographing the condition of the fundus oculi of the inspected eye.

In FIG. 1, the illuminating optical system has an illuminating light source 1 for observing the fundus oculi of the inspected eye. A beam of light radiated from the observation illuminating light source 1 is directed to a reflecting mirror 3 through a light source relay lens 2, and the light is reflected in the upper direction in FIG. 1. Thereafter, the light reflected by the reflecting mirror 3 is directed to a ring slit relay lens 6.

In this case, a strobe tube 4 functioning as a illuminating light source for photographing the fundus oculi of the inspected eye is disposed in a position conjugate to the observation illuminating light source 1 with respect to the light source relay lens 2. Also, the ring slit 5 has a slit aperture formed in a circular shape. A center of the slit aperture is positioned on an optical axis. A beam of light (a beam of light radiated from the observation illuminating light source 1 or a beam of light radiated from the strobe tube 4) transmitting through the ring slit relay lens 6 transmits through a dichroic prism 7 and is directed to an open-hole mirror 9 having an opening through another ring slit relay lens 8. A fundus oculi of an inspected eye 12 is illuminated with a beam of light reflected by the open-hole mirror 9 in the left direction in FIG. 1 through an objective lens 11. In this case, as is well-known, a working distance between the ophthalmologic apparatus according to this embodiment and the inspected eye 12 is adjusted by the function of the ring slit relay lenses 6 and 8 and the objective lens 11 so that the ring slit 5 and the cornea of the inspected eye 12 are substantially conjugate.

Figure 4:
FIG. 4 shows a slit formed on a reference mark plate shown in FIG. 1.

The reference mark projecting optical system has a light source (or a point light source) 16, for example, made of an infrared emission diode for projecting a reference mark. A reference mark plate 18 is illuminated with a beam of infrared light (shown by two-dotted chain lines in FIG. 1) radiated from the reference mark projecting light source 16 through a reference mark projecting relay lens 17a. As shown in FIG. 4, a slit having an axis extending in a longitudinal direction parallel to a paper surface of FIG. 4 is formed in the reference mark plate 18. After the infrared light transmits through the reference mark plate 18, the image is once formed, and the infrared light is directed to the dichroic prism 7 through another reference mark projecting relay lens 17b. The infrared light incident on the dichroic prism 7 is reflected in the upper direction in FIG. 1 by a reflecting surface of the dichroic prism 7, and another image is again formed in the neighborhood of the open-hole mirror 9 through the ring slit relay lens 8. A beam of infrared light reflected by the open-hole mirror 9 in the left direction in FIG. 1 transmits through the objective lens 11 and forms an image in the neighborhood of a pupil of the inspected eye 12 to illuminate the fundus oculi of the inspected eye 12 with the infrared light.

In the illuminating optical system and the reference mark projecting optical system, a beam of infrared light is reflected by the dichroic prism 7, and a beam of visible light transmits through the dichroic prism 7. Therefore, the visible light radiated from the observation light source 1 or the strobe tube 4 (that is, a photograph illuminating light source) transmits through the dichroic prism 7. In contrast, even if a beam of infrared light is included in the light radiated from the observation light source 1 or the strobe tube 4, the infrared light is reflected by the dichroic prism 7 and goes to the outside of the illuminating optical system. On the other hand, the beam of infrared light radiated from the reference mark projecting light source 16 is reflected by the dichroic prism 7.

As is shown by dotted lines in FIG. 1, after the infrared light transmitting through the slit of the reference mark plate 18 forms an image of the slit in the neighborhood of the dichroic prism 7 by the function of the reference mark projecting relay lens 17b, the infrared light is reflected in the upper direction in FIG. 1. Thereafter, the reflected light transmits through the relay lens 8 and the open-end mirror 9 and forms an image at a focal point placed on the rear side of the objective lens 11. Therefore, the light which transmits through the slit of the reference mark 18 and the objective lens 11 becomes a beam of parallel light by the objective lens 11 and is directed into the inspected eye 12. As a result, when the inspected eye 12 is an emmetropia, an image of the slit of the reference mark plate 18 is formed on the fundus oculi of the inspected eye 12. In other words, a slit image (that is, a reference mark image) of the reference mark plate 18 is defocused according to a dioptric factor of the inspected eye 12.

Figure 2:
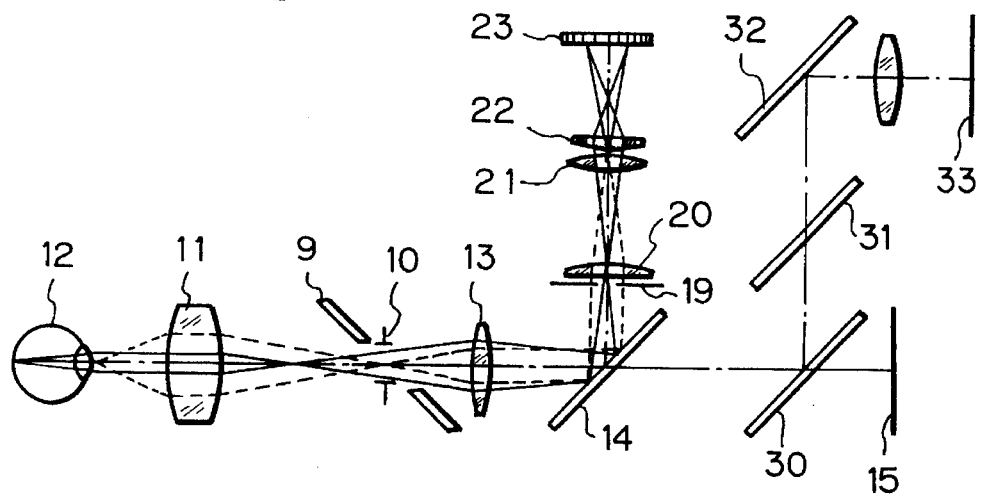
FIG. 2 is a schematic illustration of an in-focus detecting optical system of the ophthalmologic apparatus shown in FIG. 1.
Figure 3:
FIG. 3 shows an aperture of a ring slit formed on a reference mark plate shown in FIG. 1.

FIG. 2 is a schematic illustration of the in-focus detecting optical system of the ophthalmologic apparatus shown in FIG. 1.

As is shown by solid lines in FIG. 2, the slit image of the reference mark plate 18 projected on the fundus oculi of the inspected eye 12 transmits through the objective lens 11 as a beam of light radiated from a secondary light source to again form the slit image. Thereafter, the light of the slit image transmits through a central aperture of the open-hole mirror 9 and an aperture diaphragm 10 and is directed to an in-focus relay lens 13. Thereafter, the light which is radiated from the secondary light source and transmits through the in-focus relay lens 13 is directed to a dichroic mirror 14 having characteristics for reflecting a beam of infrared light and transmitting a beam of visible light. A beam of light reflected on the dichroic mirror 14 in the upper direction in FIG. 1 once forms an image in the neighborhood of a field stop 19, and the reflected light is directed to a field lens 20. Thereafter, the reflected light transmitting through the field lens 20 transmits through an image twice forming lens 21 and a pupil dividing prism 22 and is directed onto an array sensor 23.

On the other hand, a beam of reflected visible light obtained by illuminating the fundus oculi of the inspected eye 12 with the visible light radiated from the observation light source 1 or the strobe tube 4 (that is, the photographing illuminating light source) and reflecting the visible light on the fundus oculi transmits through the dichroic mirror 14 and forms an image on a photographic image plane 15. In this case, as shown in FIGS. 1 and 2, a quick returning mirror 30 is arranged between the dichroic mirror 14 and the photographic image plane 15. Therefore, the reflected visible light transmitted from the fundus oculi through the dichroic mirror 14 can be reflected in the upper direction in FIG. 1 by the quick returning mirror 30 and transmit through another dichroic mirror 31 having characteristics for reflecting a beam of infrared light and transmitting a beam of visible light. Thereafter, the reflected visible light is reflected again on a mirror 32 in the right direction in FIG. 1, transmits through an image forming lens for a television camera, and forms an observation fundus oculi image on an observation image plane 33. Therefore, the fundus oculi of the inspected eye 12 can be observed in the observation image plane 33, and the fundus oculi of the inspected eye 12 can be photographed in the photographic image plane 15.

As is described above, because the dichroic prism 7 has characteristics for reflecting a beam of infrared light and transmitting a beam of visible light, the slit image of the reference mark plate 18 formed on the fundus oculi of the inspected eye 12 is only formed of the infrared light radiated from the reference mark projecting light source 16.

Also, because the dichroic mirror 14 also has characteristics for reflecting a beam of infrared light and transmitting a beam of visible light, only the infrared light transmitting through the reference mark plate 18 which is obtained by the infrared light radiated from the reference mark projecting light source 16 reaches the array sensor 23. Therefore, the slit image (that is, the reference mark image) is formed on the array sensor 23 in a superior contrast.

In this embodiment, the field stop 19 is disposed at a conjugate position to the array sensor 23 with respect to the image twice forming lens 21. Also, the array sensor 23 is arranged at a conjugate position to the photographic image plane 15 and the observation image plane 33.

As is described above, the slit image (that is, the reference mark image) formed on the fundus oculi of the inspected eye 12 is again formed in the neighborhood of the array sensor 23 by the function of the image twice forming lens 21. In this case, a beam of light transmitting through the pupil dividing prism 22 is divided into two beams of light. The beams of light divided are focused and form different images on different areas of the array sensor 23, as shown in FIG. 2.

Figure 5:
FIG. 5 is a perspective view showing a pupil dividing prism shown in FIG. 1.

A perspective view of the pupil dividing prism 22 is shown in FIG. 5. In FIGS. 1 and 2, the pupil dividing prism 22 is shown in such an orientation that its ridgeline is in a direction perpendicular to the plane of FIGS. 1 and 2 for convenience of illustration. However, the position of the prism 22 in reality is defined by angularly displacing the prism as shown by 90 degrees. In other words, the ridgeline of the pupil dividing prism 22 is actually directed in a lateral direction which is defined by rotating the ridgeline about the optical axis by 90 degrees to make the ridgeline parallel to the plane of the drawings. As a result, the direction of the array of the cells in the array sensor 23 is actually directed in a direction perpendicular to the plane of the drawings in correspondence to the lateral direction of the ridgeline of the pupil dividing prism 22 actually directed. Therefore, the lateral direction of the ridgeline of the pupil dividing prism 22 agrees with a longitudinal direction of the slit image, and this agreement is a preferred arrangement.

Also, as is shown by dotted lines in FIG. 2, the ridgeline of the pupil dividing prism 22 is placed at a conjugate position to the aperture diaphragm 10 with respect to the in-focus relay lens 13 and the field lens 20. Because the aperture diaphragm 10 corresponds to an exit pupil in the in-focus detecting optical system, the two images formed on the array sensor 23 are formed by two different beams of light passing through two different portions of the exit pupil. Therefore, as is well-known, the two images formed on the array sensor 23 shift to lateral direction, respectively according to a so-called fore-focus condition and a so-called aft-focus condition. Accordingly, the detection of an in-focus condition between the fundus oculi of the inspected eye 12 and the ophthalmologic apparatus can be performed.

Figure 6:
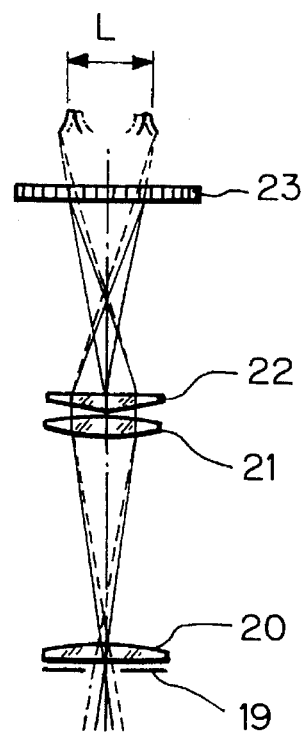
FIG. 6 is a schematic illustration showing a principle of an in-focus detection.

In detail, in such a condition that when an image distance between the two images formed on the array sensor 23 is equal to a reference distal L as shown by the solid lines in FIG. 6 in case of the in-focus condition, the image distance is, as is shown by dotted lines in FIG. 6, shorter than the reference distance L in the so-called aft-focus condition in which an accurate focusing point is placed on a rear side (that is, the upper side in FIG. 6) of the field stop 19. In contrast, the image distance is longer than the reference distance L in the so-called fore-focus condition (not shown in FIG. 6) in which an accurate focusing point is placed on a front side (that is, the lower side in FIG. 6) of the field stop 19.

Therefore, when the image distance between the two images formed on the array sensor 23 is measured to compare the image distance with the reference distance L corresponding to the in-focus condition, in-focus information can be obtained.

As shown in FIG. 1, the cells of the array sensor 23 are driven one after another according to a plurality of signals transferred from driving means 24, and a plurality of photoelectric transformed signals corresponding to the cells are output one after another from the array sensor 23 to arithmetic means 25. In the arithmetic means 25, the image distance between the two images formed on the array sensor 23 is measured according to the photoelectric transformed signals output from the array sensor 23, and the measured image distance is compared with the reference distance L to obtain a piece of in-focus information. Thereafter, a motor M is driven under control of motor driving means 26 according to the in-focus information obtained in the arithmetic means 25. By this operation, the in-focus relay lens 13 is appropriately moved along the optical axis and, therefore, on the array sensor 23, and thus, the photographic image plane 15 and the observation image plane 33, the images of the fundus oculi of the inspected eye 12 are focused.

Next, the positional adjustment detecting optical system in which a positional adjustment between the ophthalmologic apparatus and the inspected eye 12 is performed by utilizing a beam of light which is radiated from the reference mark projecting optical system and is projected on the fundus oculi of the inspected eye 12 is described.

Figures 7, 8:
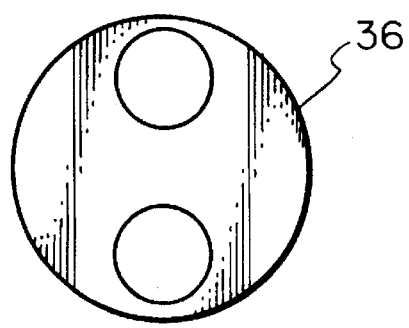
FIG. 7 shows a pair of apertures formed in a pupil dividing diaphragm shown in FIG. 1.
FIG. 8 is an illustration showing a positional adjustment between an inspected eye and the ophthalmologic apparatus.

In FIG. 1, a beam of infrared light radiated from the reference mark projecting optical system is reflected by the cornea of the inspected eye 12 and transmits through a lens 34 and a mirror, and an image is once formed. Thereafter, the beam of infrared light transmits through a relay lens 35, a pupil dividing diaphragm 36 and another relay lens 37 in this order. As shown in FIG. 7, the pupil dividing diaphragm 36 has a pair of apertures formed in a circular shape. Therefore, as is well-known in ophthalmometers (keratometer) or the like, the infrared light reflected by the cornea of the inspected eye 12 is pupil-divided into two beams of infrared light by the function of the pupil dividing diaphragm 36. The two beams of infrared light pupil-divided are reflected by the dichroic mirror 31 having the characteristics for reflecting a beam of infrared light and transmitting a beam of visible light and is lead to the observation image plane 33, and two reference mark images formed by the two beams of infrared light are observed.

As shown in FIG. 8, when a positional adjustment between the ophthalmologic apparatus and the inspected eye 12 is appropriate and a positional relationship between the ophthalmologic apparatus and the inspected eye 12 is adjusted such that any flare caused by light reflected by the cornea of the eye lens of the inspected eye 12 is not directed to the observation image plane 33, the two beams of infrared light are directed on the same area of the observation image plane 33. Therefore, a single reference mark image is observed. In contract, when the positional adjustment is not appropriate, the two beams of infrared light are directed on different areas of the observation image plane 33. Therefore, two reference mark images separated from each other are observed. Accordingly, by slightly moving the ophthalmologic apparatus to a place where the two beams of infrared light are directed to the same area of the observation image plane 33, the positional adjustment between the ophthalmologic apparatus and inspected eye 12 can be appropriately performed.

In the above-mentioned embodiment, the infrared light is used as a beam of reference mark projecting light. However, it is applicable that a beam of near infrared light be used as the reference mark projecting light. In this case, it is required to appropriately change the characteristics of the dichroic prism and the dichroic mirrors and according to a wavelength of the near infrared light used as the reference mark projecting light. In case where the near infrared light is used as the reference mark projecting light, the reference mark can be observed by an operator's own eye when an ocular lens is used in the observation system. That is, not only the operator can confirm with his own eye whether or not the reference mark image is projected on a prescribed position of the fundus oculi on which the operator intends to focus the ophthalmologic apparatus, but also the operator can confirm the positional adjustment between the ophthalmologic apparatus and the inspected eye 12 with his own eye.

It is apparent that the light source 16 of the reference mark projecting optical system is put out when the fundus oculi of the inspected eye 12 is photographed. Also, when the ophthalmologic apparatus is placed at an appropriate position by performing the positional adjustment in the positional adjustment detecting optical system and the observation fundus oculi image is observed in focus on the observation image plane 33 by performing the in-focus detection in the in-focus detecting optical system, it may happen that it is difficult to observe the observation fundus oculi image because the image of the reference mark image overlaps with the observation fundus oculi image. In this case, by putting out the light source 16 of the reference mark projecting optical system the fundus oculi image can be observed in high visibility. That is, it is preferred that the ophthalmologic apparatus further comprises means for appropriately putting out the light source 16 of the reference mark projecting optical system.

Also, in the above-mentioned embodiment, the infrared light is used as a beam of reference mark projecting light, and the dichroic mirror 14 has the characteristics for reflecting a beam of infrared light and transmitting a beam of visible light. However, it is applicable that the dichroic mirror 14 have characteristics for semi-transmitting (or semi-reflecting) for a beam of infrared light and transmitting a beam of visible light. In this case, it is possible to observe the reference mark image by using, for example, a TV monitor in the observing optical system. Therefore, not only an operator can confirm the in-focus condition through the TV monitor with his own eye, but also the operator can confirm through the TV monitor with his own eye whether or not the reference mark image is projected on a prescribed position of the fundus oculi on which the operator intends to focus the ophthalmologic apparatus.

As is described above, in the ophthalmologic apparatus according to the present invention, because the reference mark projecting light source 16 is utilized as a detecting light source to detect the in-focus condition in the in-focus detecting optical system and the positional adjustment in the positional adjustment detecting optical system, the construction of the ophthalmologic apparatus can be simplified. Moreover, the detection of the in-focus condition and the positional adjustment can be easily and rapidly performed, and the photograph of the fundus oculi of the inspected eye 12 can be obtained in high quality.

What is claimed is:

1. An ophthalmologic apparatus, comprising:
   an illuminating optical system for illuminating a fundus oculi of an inspected eye;
   a photographing and observing optical system for photographing and observing the fundus oculi of the inspected eye;
   a reference mark projecting optical system for projecting a reference mark on the fundus oculi of the inspected eye;
   an in-focus information detecting system for detecting in-focus information between the photographing and observing optical system and the fundus oculi of the inspected eye by receiving light from an image of the reference mark projected on the fundus oculi of the inspected eye by the reference mark projecting optical system; and
   a positional adjustment information detecting system for detecting positional adjustment information representing a positional adjustment between the ophthalmologic apparatus and the inspected eye by receiving light which is radiated from the reference mark projecting optical system and reflected by a cornea of the inspected eye.

2. An ophthalmologic apparatus according to claim 1 in which the reference mark projecting optical system comprises a light source for radiating at least one of a beam of infrared light and a beam of near infrared light.

3. An ophthalmologic apparatus according to claim 1 or 2 in which the positional adjustment information detecting system comprises:
   a pupil dividing diaphragm for dividing the beam of light, which is radiated from the reference mark projecting optical system and reflected by the cornea of the inspected eye, into two beams of light; and
   an observing system for observing the two beams of light divided by the pupil dividing diaphragm.

4. An ophthalmologic apparatus according to claim 3 in which the two beams of light which are divided by the pupil dividing diaphragm overlap with each other in the observing system of the positional adjustment information detecting system when a desired positional adjustment between the ophthalmologic apparatus and the inspected eye is attained.

5. An ophthalmologic apparatus according to claim 3 in which the observing system constitutes a part of the photographing and observing optical system.

6. An ophthalmologic apparatus according to claim 1 in which the in-focus information detecting system comprises:

a pupil dividing prism for dividing a beam of light directed thereto into two beams of light; and an array sensor for receiving the two beams of light divided by the pupil dividing prism.

7. An ophthalmologic apparatus according to claim 6 in which the in-focus information detecting system further comprises:

an optical element for preventing a beam of light other than the beam of infrared light or the beam of near infrared light from transmitting through the optical element, said optical element being disposed in front of said pupil dividing prism.

* * * * *